United States Patent [19]

Birbaum et al.

[11] Patent Number: 5,189,084
[45] Date of Patent: Feb. 23, 1993

[54] PROCESS FOR INCORPORATING O-HYDROXYPHENYL-S-TRIAZINES IN ORGANIC POLYMERS

[75] Inventors: Jean-Luc Birbaum, Fribourg; Jean Rody, Riehen; Mario Slongo, Tafers, all of Switzerland; Andreas Valet, Eimeldingen, Fed. Rep. of Germany

[73] Assignee: Ciba-Geigy Corporation, Ardsley, N.Y.

[21] Appl. No.: 841,907

[22] Filed: Feb. 26, 1992

Related U.S. Application Data

[63] Continuation of Ser. No. 628,274, Dec. 14, 1990, abandoned.

[30] Foreign Application Priority Data

Dec. 21, 1989 [CH] Switzerland ............... 4581/89

[51] Int. Cl.$^5$ .................... C08K 5/34; C08C 19/22; C08G 12/30
[52] U.S. Cl. .................... 524/100; 524/720; 525/374; 525/380; 528/62; 528/96; 528/332
[58] Field of Search .............. 524/100, 720, 99; 525/374, 380; 528/62, 96, 332

[56] References Cited

U.S. PATENT DOCUMENTS

| | | | |
|---|---|---|---|
| 3,118,887 | 1/1964 | Hardy et al. | 524/929 |
| 3,244,708 | 4/1966 | Duennenberger et al. | 524/100 |
| 3,423,360 | 1/1969 | Huber et al. | 524/100 |
| 3,896,125 | 7/1975 | Helmo et al. | 564/225 |
| 4,210,612 | 7/1980 | Karrer | 526/262 |
| 4,234,728 | 11/1980 | Rody et al. | 524/100 |
| 4,294,949 | 10/1981 | Karrer | 526/262 |
| 4,356,287 | 10/1982 | Loffelman et al. | 524/100 |
| 4,414,372 | 11/1983 | Farrham et al. | 526/190 |
| 4,695,607 | 9/1987 | Spinelli | 525/272 |
| 4,826,978 | 5/1989 | Migdal et al. | 524/100 |
| 4,880,859 | 11/1989 | Slongo et al. | 524/99 |
| 4,962,142 | 10/1990 | Migdal et al. | 524/100 |
| 4,972,009 | 11/1990 | Suhadolnik | 524/100 |

Primary Examiner—Paul R. Michl
Assistant Examiner—Peter Szekely
Attorney, Agent, or Firm—Luther A. R. Hall; Harry Falber; William A. Teoli, Jr.

[57] ABSTRACT o-Hydroxyohenyl-s-triazines containing suitable functional groups are incorporated in polymers by copolymerisation, copolycondensation, copolyaddition or by polymer-analogous reaction. The modified polymers so obtained have excellent stability to degradation induced by light, oxygen and heat. They can also be used as stabilisers.

25 Claims, No Drawings

PROCESS FOR INCORPORATING O-HYDROXYPHENYL-S-TRIAZINES IN ORGANIC POLYMERS

This application is a continuation of application Ser. No. 628,274, filed Dec. 14, 1990 now abandoned.

The present invention relates to a process for incorporating o-hydroxyphenyl-s-triazines in organic polymers and to the modified polymers obtainable by said process.

It is common knowledge that o-hydroxyphenyl-s-triazines absorb UV light and, by virtue of this property, can be used as light stabilisers for organic materials, especially for organic polymers. For this purpose it is preferred to use those compounds which contain a p-alkoxy group in addition to the o-hydroxy group, which alkoxy group may also be substituted, as taught, for example, in U.S. Pat. Nos. 3,118,887 or 3,244,708.

To prevent migration and elution of these stabilisers, it has also already been proposed to incorporate in the polymers to be protected p-acryloyloxy derivatives of o-hydroxyphenyl-s-triazines by copolymerisation or by grafting, as taught in U.S. Pat. No. 3,423,360. These p-acryloyloxy derivatives, however, have a propensity to yellowing when exposed to UV light.

The search for o-hydroxyphenyl-s-triazine derivatives suitable for chemical incorporation has led to the discovery of a substantial number of derivatives which can be incorporated in different types of organic polymers by copolymerisation, co-polycondensation, co-polyaddition or by polymer-analogous reaction, and which, after incorporation, have a lesser tendency to yellowing than the aforementioned derivatives.

The present invention accordingly relates to a process for incorporating o-hydroxyphenyl-s-triazines in organic polymers, which process comprises incorporating a compound of formula I

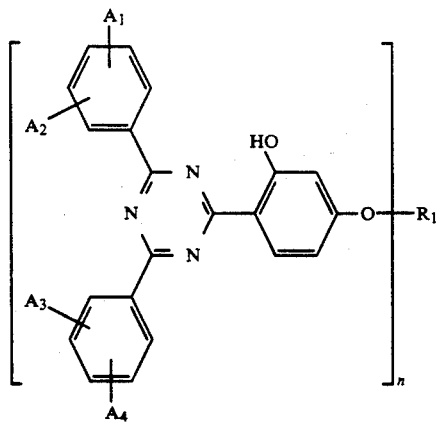

wherein
n is 1 or 2,
$A_1$, $A_2$, $A_3$ and $A_4$ are each independently of one another hydrogen, $C_1$-$C_{12}$alkyl, cyclohexyl or halogen,
$R_1$, when n is 1, is hydrogen, $C_1$-$C_{18}$alkyl which is substituted by OH, —COOH, —COOR$_2$, —NHR$_3$, —CONHR$_4$,

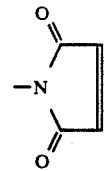

and/or —O—CO—R$_4$, $C_4$-$C_{20}$alkyl which is substituted by OH and interrupted by one or more oxygen atoms, $C_2$-$C_4$alkyl which is substituted by OH and $C_1$-$C_{12}$alkoxy or phenoxy, cyclohexyl which is substituted by OH or —OCOR$_4$, or is $C_2$-$C_6$alkenyl, glycidyl or a group selected from

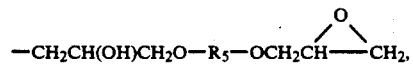

—CO—R$_6$—COOH or —CO—NH—R$_7$—NCO, and, when n is 2, is a group selected from —CH$_2$CH(OH)CH$_2$—, —CO—CH=CH—CO—, —CH$_2$CH(OH)CH$_2$O—R$_5$—OCH$_2$CH(OH)CH$_2$— or —CH$_2$CH(R$_8$)O—CO—CH=CH—CO—OCH(R$_8$)CH$_2$—,
$R_2$ is $C_1$-$C_4$alkyl, glycidyl or $C_3$-$C_5$alkenyl,
$R_3$ is hydrogen, $C_1$-$C_{12}$alkyl, $C_3$-$C_5$alkenyl or cyclohexyl,
$R_4$ is $C_2$-$C_6$alkenyl or $C_2$-$C_6$hydroxyalkyl,
$R_5$ is $C_2$-$C_{10}$alkylene, phenylene or a group

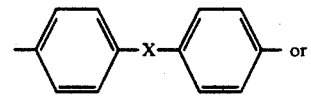

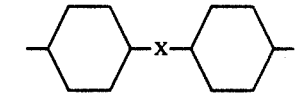

wherein X is —O—, —S—, —SO$_2$, —CH$_2$— or —C(CH$_3$)$_2$—, or R$_5$ is a group —CO—R$_9$—CO—,
$R_6$ is $C_2$-$C_{14}$alkylene, —CH=CH— or o-phenylene,
$R_7$ is $C_2$-$C_{10}$alkylene, phenylene, tolylene or a group of formula

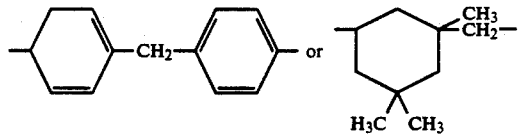

$R_8$ is hydrogen or methyl, and
$R_9$ is $C_2$-$C_{10}$alkylene, —CH=CH— or phenylene,
either during the synthesis of the polymer by copolymerisation, copolycondensation or copolyaddition, or by reaction with a polymer which contains suitable functional groups.

$A_1$, $A_2$, $A_3$, $A_4$ and $R_3$ as $C_1$-$C_{12}$alkyl may be unbranched or branched alkyl such as methyl, ethyl, isopropyl, n-butyl, sec-butyl, tert-butyl, pentyl, hexyl, heptyl, octyl, 2-ethylhexyl, di-tert-octyl, decyl or dodecyl.

$R_1$ and $R_4$ as $C_2$-$C_6$alkenyl may be vinyl, 1-propenyl, allyl, methallyl, 2-butenyl or 2-hexenyl. $R_2$ and $R_3$ as $C_3$-$C_5$alkenyl are preferably allyl or methallyl. $R_2$ as $C_1$-$C_4$alkyl is preferably methyl or ethyl.

$R_4$ as $C_2$-$C_6$hydroxyalkyl is preferably 2-hydroxyethyl or 2-hydroxypropyl.

$R_5$, $R_7$ and $R_9$ as $C_2$-$C_{10}$alkylene may be 1,2-ethylene, trimethylene, tetramethylene, hexamethylene, octamethylene or 1,3,3-trimethyltetramethylene. $R_6$ as $C_2$-$C_{14}$alkylene is preferably 1,2-alkylene such as 1,2-ethylene, 1,2-propylene, 1,2-octylene or 1,2-dodecylene.

$R_1$ as substituted $C_1$-$C_{18}$alkyl is preferably substituted $C_1$-$C_4$alkyl. It may contain one or more substituents selected from the group consisting of OH, —COOH, —COOR$_2$, —NHR$_3$, —CONHR$_4$ and —O—CO—R$_4$. Exemplary are 2-hydroxyethyl, 2-hydroxypropyl, 2-hydroxybutyl, carboxymethyl, 2-carboxyethyl, 2-carboxypropyl, methoxycarbonylmethyl, methoxycarbonylethyl, ethoxycarbonylethyl, glycidyloxycarbonylethyl, allyloxycarbonylmethyl, allyloxycarbonylethyl, 2-aminoethyl, 2-hydroxy-3-methylaminopropyl, 2-hydroxy-3-butylaminopropyl, 2-hydroxy-3-allylaminopropyl, 2-(allylaminocarbonyl)ethyl, 2-hydroxyethylaminocarbonylmethyl, 2-acryloyloxyethyl, methacryloyloxymethyl, 2-hydroxy-3-acryloyloxypropyl, 2-hydroxy-3-methacryloyloxypropyl, 2-hydroxy-3-maleimidopropyl or 2,3-dihydroxypropyl.

$R_1$ as $C_4$-$C_{20}$alkyl which is substituted by OH and interrupted by one or more oxygen atoms may be a $-(CH_2CH_2O)_m H$ group in which m=2-10 or a

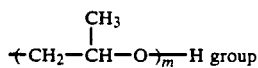

group in which m=2-6.

$R_1$ as $C_2$-$C_4$alkyl which is substituted by OH and $C_1$-$C_{12}$alkoxy or phenoxy is preferably correspondingly substituted propyl, and is, typically, 2-hydroxy-2-butoxypropyl, 2-hydroxy-3-hexyloxypropyl, 2-hydroxy-3-octyloxypropyl, 2-hydroxy-3-dodecyloxypropyl or 2-hydroxy-3-phenoxypropyl.

Where $R_1$ is cyclohexyl which is substituted by OH or —OCOR$_4$, the OH or —OCOR$_4$ group is preferably in ortho-position (2-position).

It is preferred to use for incorporation a compound of formula I, wherein n is 1 or 2, $A_1$, $A_2$, $A_3$ and $A_4$ are hydrogen, $C_1$-$C_4$alkyl or chloro, $R_1$, when n is 1, is hydrogen, $C_1$-$C_4$alkyl which is substituted by OH, —COOH, —COOR$_2$, —NHR$_3$, —CONHR$_4$ and/or —O—CO—R$_4$, $C_4$-$C_{20}$alkyl which is substituted by OH and interrupted by one or more oxygen atoms, propyl which is substituted by OH and $C_1$-$C_{12}$alkoxy or phenoxy, cyclohexyl which is substituted by OH or —OCOR$_4$, or is allyl, glycidyl or a

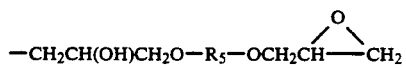

or —CO—NH—R$_7$—NCO group, and, when n is 2, is a group selected from —CH$_2$CH(OH)CH$_2$—, —CH$_2$CH(OH)CH$_2$O—R$_5$—OCH$_2$CH(OH)CH$_2$— or —CH$_2$CH(R$_8$)O—CO—CH=CH—CO—OCH(R$_8$)CH$_2$—, $R_2$ is $C_1$-$C_4$alkyl, glycidyl or allyl, $R_3$ is $C_1$-$C_{12}$alkyl, $R_4$ is $C_2$-$C_6$alkenyl, $R_5$ is $C_2$-$C_{10}$alkylene, phenylene or a

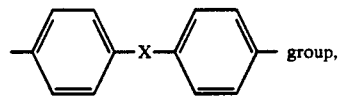

wherein X is —O—, —S—, —SO$_2$, —CH$_2$— or —C(CH$_3$)$_2$—, or R$_5$ is a —CO—R$_9$—CO— group, $R_7$ is $C_2$-$C_{10}$alkylene, phenylene, tolylene or a group of formula

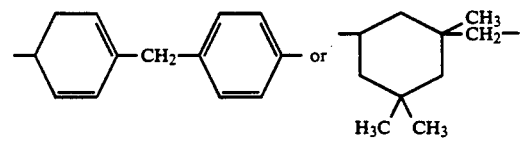

$R_8$ is hydrogen or methyl, and $R_9$ is $C_2$-$C_{10}$alkylene, —CH=CH— or phenylene.

It is particularly preferred to incorporate a compound of formula I, wherein n is 1 or 2, $A_1$ and $A_3$ are hydrogen, methyl or chloro, $A_2$ and $A_4$ are hydrogen or methyl, $R_1$, when n is 1, is hydrogen, $C_1$-$C_4$alkyl which is substituted by OH, —COOH, —COOR$_2$ and/or —O—CO—R$_4$, $C_4$-$C_{20}$alkyl which is substituted by OH and interrupted by one or more oxygen atoms, propyl which is substituted by OH and $C_4$-$C_{12}$alkoxy, or is glycidyl, allyl, or a

and, when n is 2, is a —CH$_2$CH(OH)CH$_2$— or —CH$_2$CH(OH)CH$_2$O—R$_5$—OCH$_2$CH(OH)CH$_2$— group, $R_2$ is $C_1$-$C_4$alkyl or allyl bedeutet, $R_4$ is $C_2$-$C_4$alkenyl, and $R_5$ is $C_4$-$C_8$alkylene or

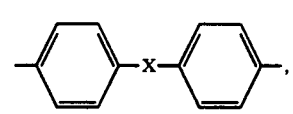

wherein X is —CH$_2$— or —C(CH$_3$)$_2$—.

Incorporation can be effected by copolymerisation, copolycondensation or copolyaddition or by reaction with a polymer which carries suitable functional groups.

Those compounds of formula I which contain ethylenically unsaturated groups are especially suitable for incorporation by copolymerisation. These are compounds of formula I, wherein n is 1 or 2, $R_1$, when n is 1, is $C_2$-$C_6$alkenyl, $C_1$-$C_{18}$alkyl which is substituted by —COOR$_2$, —NH—R$_3$, —CONHR$_4$ or —O—CO—R$_4$, cyclohexyl which is substituted by —O—CO—R$_4$, or is a —CO—CH=CH—COOH group, and, when n=2, is group selected from —CO—CH=CH—CO—, —CH$_2$CH(R$_8$)O—CO—CH=CH—CO—OCH(R$_8$)C-

$H_2$— or —$CH_2CH(OH)CH_2O$—CO—CH=CH—CO—$OCH_2CH(CH)CH_2$—, $R_2$ is $C_3$-$C_5$alkenyl, $R_3$ is allyl, $R_4$ is $C_2$-$C_6$alkenyl, and $R_8$ is hydrogen or methyl.

Particularly suitable for incorporation are compounds of formula I, wherein $R_1$ is allyl, $C_1$-$C_4$alkyl which is substituted by —$COOR_2$ or —O—CO—$R_4$, or cyclohexyl which is substituted by —O—CO—$R_4$, $R_2$ is allyl, and $R_4$ is $C_2$-$C_4$alkenyl.

The compounds of formula I can be incorporated by copolymerisation in those polymers which are prepared by polymerisation of ethylenically unsaturated monomers. These monomers comprise typically the following monomers: acrylic acid, methacrylic acid, esters of acrylic acid and methacrylic acid, amides of acrylic acid and methacrylic acid, acrylonitrile, styrene, α-methylstyrene, butadiene, isoprene, maleic anhydride, esters, amides and imides of maleic acid, vinyl chloride, vinylidene chloride, vinyl acetate, vinyl butyrate, vinyl alkyl ether or N-vinylpyrrolidone. It is preferred to incorporate the compounds of formula I in those polymers which are derived from acrylic acid or methacrylic acid, esters or amides of acrylic acid or methacrylic acid, styrene or acrylonitrile. The polymer can also be derived from one or more such monomers. The addition of the unsaturated compound of formula I is made during the polymerisation so that copolymerisation takes place.

Polymerisation can be initiated by radical, anionic or cationic initiators. It is preferred to use radical initiators which, on the application of heat, decompose into radicals, for example organic peroxides or hydroperoxides, azo compounds or redox catalysts. Polymerisation can also be initiated by energy-rich radiation, for example also in the case of photocurable paints or lacquers (UV curable or ESR curable). The copolymerisable hydroxyphenyl-s-triazine is in this case incorporated in the paint matrix during the film formation.

Especially suitable for such copolymerisation reactions is the method of group transfer polymerisation, in which a "living" polymer is formed by using specific initiators. Examplary of initiators suitable for this method are 1-trimethylsiloxy-1-alkoxy-2-methylpropenes. The method of group transfer polymerisation has been known for some years and is disclosed, for example, in U.S. Pat. Nos. 4,695,607 and 4,414,372.

The polymerisation can be carried out in solution, emulsion, dispersion or in the melt. These methods are known to the skilled person. These copolymerisations are described in detail in the subsequent Examples.

Particularly suitable compounds for incorporation by copolycondensation or copolyaddition are those compounds of formula I which contain two functional groups. These are, typically, the compounds of formula I in which n is 1 or 2, $R_1$, when n is 1, is $C_1$-$C_{18}$alkyl which is substituted by OH and —COOH, —$COOR_2$ or —$NHR_3$, or is a —$CH_2CH(OH)CH_2OH$ or

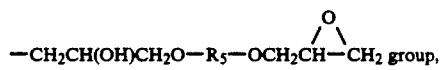
—$CH_2CH(OH)CH_2O$—$R_5$—$OCH_2CH$—$CH_2$ group, and, when n is 2, is a —$CH_2CH(OH)CH_2O$—$R_5$—$OCH_2CH(OH)CH_2$— group, $R_2$ is $C_1$-$C_4$alkyl, $R_3$ is hydrogen, $C_1$-$C_{12}$alkyl, allyl or cyclohexyl, and $R_5$ is $C_2$-$C_{10}$alkylene, phenylene or a group

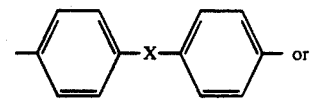

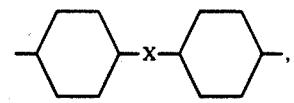

wherein X is —O—, —S—, —$SO_2$—, —$CH_2$— or —$CH(CH_3)_2$—. If it is desired to incorporate only minor amounts of a compound of formula I by polycondensation or polyaddition, then those compounds of formula I which contain only one functional group, for example a —OH, —COOH, —$COOR_2$, —$NHR_3$ or

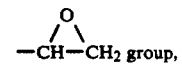
—CH—$CH_2$ group, are especially suitable.

These compounds are in particular those compounds of formula I, wherein n is 1, $R_1$ is hydrogen, $C_1$-$C_{18}$alkyl which is substituted by OH, —COOH, —$COOR_2$, —$NHR_3$, —$CONHR_4$ or —O—CO—$R_4$, $C_4$-$C_{20}$alkyl which is substituted by OH and interrupted by one or more oxygen atoms, $C_2$-$C_4$-Alkyl which is substituted by OH and $C_1$-$C_{12}$alkoxy or phenoxy, OH-substituted cyclohexyl, or is glycidyl or a —CO—$R_6$—COOH or —CO—NH—$R_7$—NCO group, $R_2$ is $C_1$-$C_4$alkyl or glycidyl, $R_3$ is hydrogen, $C_1$-$C_{12}$alkyl or cyclohexyl, $R_4$ is $C_2$-$C_6$hydroxyalkyl, $R_6$ is $C_2$-$C_{14}$alkylene, —CH=CH— or o-phenylene, and $R_7$ is as defined in claim 1.

Such mono- or difunctional compounds of formula I can be incorporated in, for example, polyesters, polyether esters, polyamides, polyurethanes, polycarbonates, epoxy resins, phenolic resins, melamine resins or alkyd resins. Incorporation is made by addition during the synthesis of the condensation or addition polymers by the methods known to the skilled person.

The compounds of formula I can also be incorporated in oligomer or polymer intermediates. For example, unsaturated compounds of formula I can be added to unsaturated polyester resins and mixtures thereof with other vinyl compounds, and then cured by addition of radical initiators. Alternatively, oligomer epoxy resins can be reacted with functional compounds of formula I and then cured with an epoxy hardener. Or else OH functional compounds of formula I can be reacted with melamine resins and the resultant compounds subsequently cured by addition of acrylate resins.

Incorporation of the compounds of formula I can also be effected with a precursor before the final cure of the resin. The resin can also be cured by acid or basic catalysis without the triazines interfering in the reaction.

A further means of incorporation consists in the reaction of a compound of formula I with a polymer which contains suitable functional groups. Such polymers may be, for example, polymers which contain hydroxyl, carboxyl, anhydride, amino, epoxy or isocyanate groups. Exemplary of these polymers are copolymers of acrylic and methacrylic acid, of hydroxyalkyl (meth)acrylates, of glycidyl (meth)acrylates, partially hydrolysed polyvinyl acetate or ethylene-vinyl acetate copolymer, partially esterified cellulose, partially hydrolysed polyalkyl (meth)acrylates, polyesters or polyurethanes carrying reactive end groups, epoxy resins or copolymers of maleic acid, of maleic anhydride or of half-esters or half-amides of maleic acid.

Those compounds of formula I are suitable for the reaction which contain a functional group which is able to react with the functional groups of the polymer. These groups may be hydroxyl, carboxyl, ester, amino, epoxy or isocyanate groups. If it is desired to modify, for example, a polymer which contains OH groups with a compound of formula I, then a compound of formula I may be used which contains at least one isocyanate, epoxy, carboxyl or ester group. A polymer which contains epoxy groups can be reacted with, for example, a compound of formula I which contains at least one hydroxyl, carboxyl or amino group. A copolymer of maleic anhydride can be reacted with, for example, a compound of formula I which contains a hydroxyl, amino or epoxy group.

These reactions are carried out by the methods conventionally employed for polymer-analogous reactions. The reaction is preferably carried out in solution. All or only some of the functional groups of the polymer can be reacted. The amount of compound of formula I used for the reaction will depend thereon. Such reactions are described in the subsequent Examples.

A special method of incorporating the compounds of formula I in polymers is grafting ethylenically unsaturated derivatives of formula I on to hydrocarbon polymers. The compounds of formula I which contain ethylenically unsaturated groups have previously been defined in detail. Hydrocarbon polymers may be saturated or unsaturated. Saturated hydrocarbon polymers are, typically, polyolefins such as polyethylene, polypropylene, polybutene or polyisobutene. Unsaturated hydrocarbons comprise the diene polymers and their copolymers with olefins, typically polybutadiene, polyisoprene, propylene/butadiene or ethylene/propylene/butadiene. Grafting on polyolefins, especially on polyethylene, is preferred.

The grafting reaction can be carried out in solution or in the melt. The catalysts employed are the radical formers also used for the homo- or copolymerisation of unsaturated compounds.

All these methods of incorporating compounds of formula I in polymers can be carried out with a fairly small amount of triazine, typically with 0.05 to 5% by weight, based on the modified polymer. These amounts impart to the polymers stability to degradation induced by light, oxygen and heat, which stability is not lost through migration or elution of the stabiliser. For this utility it is preferred to incorporate 0.1 to 3% by weight of a compound of formula I.

It is, however, also possible by this method to incorporate larger amounts of the triazine, for example 5 to 50% by weight, based on the modified polymer. This is useful if it is intended to use the modified polymers as polymer stabilisers. These polymer stabilisers can be added to organic materials, preferably organic polymers. The polymer stabilisers can also be applied as a thin protective layer to plastic moulded articles, for example in dissolved form or by co-extrusion as disclosed, for example, in U.S. Pat. No. 4,676,870.

A further utility of this process is the incorporation of compounds of formula I in polymer microparticles. The incorporation of light stabilisers by copolymerisation or copolycondensation in such microparticles which can be used as disperse phase in coatings is disclosed in EP-A-226 538. In this method, 0.1 to 30%, preferably 0.5 to 10% by weight, of a compound of formula I, based on the modified polymer, is incorporated in the microparticles.

The method of group transfer polymerisation described, for example, in EP-A-293 871 may conveniently be used for the incorporation of compounds of formula I in microparticles.

The invention also relates to the modified polymers obtained by the method described above, which polymers contain a compound of formula I in the specified amounts by weight in chemically bound form and which are thereby stabilised against degradation induced by light, oxygen and heat.

The modified polymers may contain different additives, as is customary in the polymer art. These additives may be stabilisers or processing auxiliaries, or pigments or other modifiers. The following additives are illustrative of those which may be used:

1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example 4-hydroxylauranilide, 4-hydroxystearanilide, 2,4-bis(octylmercapto)-6-(3,5-di-tert-butyl-4-hydroxyanilino)-s-trazine, 1(2-hydroxoctyl N-(3,5-di-tert-butyl-4-hydroxyphenyl)carbamate.

1.7. Esters of β-(3,5-di-tert-butyl-4-hydroxyphenyl)-propionic acid with mono- or polyhydric alcohols, e.g. with methanol, octadecanol, 1,6-hexanediol, neopentyl glycol, triethylene glycol, pentaerythritol, tris(hydroxyethyl) isocyanurate, thiodiethylene glycol, N,N'-bis(-hydroxyethyl)oxalodiamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

1.9. Esters of β-(3,5-dicyclohexyl-4-hydroxyphenyl)-propionic acid with mono- or poly-hydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec- butyl-5'-tert-butyl, 4'-octoxy, 3',5'-di-tert-amyl and 3',5'-bis(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy- cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methyl-phenyl undecyl ketoneoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxy-benzylmalonate, the condensation product of 1(2-hydroxyethyl)-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tetrakis(2,2,6,6-tetramethyl-4-piperidyl)-1,2,3,4-butanetetraoate, 1,1'-(1,2-ethanediyl)bis-(3,3,5,5-tetramethylpiperazinone), bis(2,2,6,6-tetramethylpiperidyl)succinate, bis(1-octyloxy-2,2,6,6-tetramethylpiperidyl)sebacate.

2.7. Oxalyl diamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butoxanilide and mixtures of ortho- and para-methoxy-disubstituted oxanilides and mixtures of o- and p-ethoxydisubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)-1,3,5-triazine, 2-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalyl diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-ditertbutylphenyl) pentaerythritol diphosphite, tristearyl sorbitol triphosphite, tetrakis-(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in conjunction with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, fluorescent whitening agents, flameproofing agents, antistatic agents and blowing agents.

The addition of sterically hindered amines (section 2.6 of the above list) is to be singled out for special mention, as they impart a particularly effective light stabilisation to the modified polymers.

If the additives are stabilisers, they are preferably added in a total amount of 0.05 to 5% by weight.

A further embodiment of the invention comprises incorporating a further stabiliser in the polymer in addition to a compound of formula I. The additional incorporation of a sterically hindered amine is of particular importance. Depending on whether the sterically hindered amine used contains an ethylenically unsaturated group or another functional group, incorporation is effected by copolymerisation or copolycondensation or copolyaddition, or by reaction with a polymer which contains suitable functional groups.

Sterically hindered amines which contain unsaturated groups and are suitable in the practice of this invention for copolymerisation, are the acrylic and methacrylic acid derivatives of 2,2,6,6-tetramethylpiperidine disclosed, for example, in U.S. Pat. No. 3,705,166, and the N-alkyl and N-alkoxy derivatives thereof. Further copolymerisable derivatives of tetramethylpiperidine are disclosed in U.S. Pat. No. 4,210,612 and in EP-A-389 420.

Sterically hindered amines which are able to react with functional polymers are typically those which contain hydroxyl groups, for example 2,2,6,6-tetramethylpiperidin-4-ol, 1,2,2,6,6-pentamethylpiperidin-4-ol, 1-hydroxyethyl-2,2,6,6-tetramethylpiperidin-4-ol or the compounds disclosed in U.S. Pat. No. 4,087,404 and in EP-A 389 419; or those which contain amino groups such as 4-amino-2,2,6,6-tetramethylpiperidine or the 4-aminopiperidines disclosed in U.S. Pat. No. 3,904,581.

The incorporation of such sterically hindered amines can be effected simultaneously with the incorporation of the triazines of formula I, or beforehand or subsequently. The methods employed are the same as those for the incorporation of the triazines. Further details will be found in the subsequent Examples.

If it is desired to incorporate a sterically hindered amine in addition to the triazine of formula I in the polymer, then said amine is preferably added in an amount corresponding to 0.1 to 15% by weight, based on the modified polymer.

The polymers modified in the practice of this invention may be used for the conventional end-use forms of polymers, for example as moulded articles, pipes, boards, sheets, filaments, casting resins, adhesives or coatings. The preferred utility is as binders for paints and lacquers which may be pigmented or unpigmented.

The modified polymers may also be used as stabilisers for organic materials, mainly for polymers. For this utility it is preferred to use those modified polymers in which at least 5% of a compound of formula I has been incorporated. These modified polymers may be used for stabilising organic materials such as oils, fats, waxes, cosmetics or photographic materials. Preferably, however, they are used for stabilising organic polymers. Representative examples of polymers which may be so stabilised are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned in 1) above, for example polypropylene/ethylene propylene copolymers, LDPE/EVA, LDPE/EAA, LLDPE/EVA and LLDPE/EAA.

3a. Hydrocarbon resins (for example $C_5$–$C_9$), including hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, for example styrenel[ch-]butadiene, styrene/acrylonitrile, styrene/alkylmethacrylate, styrene/butadiene/alkylacrylate, styrene/ maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or α-methylstyrene, for example styrene on polybutadiene, styrene on polybutadiene/styrene or polybutadiene/acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyalkylacrylates or polyalkylmethacrylates, styrene and acrylonitrile on acrylate/butadiene copolymers, as well as mixtures thereof with the copolymers listed under 5), for example the copolymer mixtures known as ABS, MBS, ASA or AES polymers.

7. Halogenated polymers such as polychloroprene, chlorinated rubbers, chlorinated or sulfochlorinated polyethylene, copolymers of ethylene and chlorinated ethylene, epichlorohydrin homo- and copolymers, preferably polymers of halogenated vinyl compounds, for example poly- vinylchloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkylacrylate copolymers, acrylonitrile/alkoxyalkylacrylate or acrylonitrile/vinyl halide copolymers or acrylonitrile/alkylmethacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyrate, polyallyl phthalate or polyallylmelamine; as well as their copolymers with the olefins mentioned in 1) above.

11. Homopolymers and copolymers of cyclic ethers such as polyalkylene glycols, polyethylene oxide, polypropylene oxide or copolymers thereof with bisglycidyl ethers.

12. Polyacetals such as polyoxymethylene and those polyoxymethylenes which contain ethylene oxide as a comonomer; polycetals modified with thermoplastic polyurethanes, acrylates or MBS.

13. Polyphenylene oxides and sulfides and mixtures thereof with polystyrene or polyamides.

14. Polyurethanes which are derived from polyethers, polyesters or polybutadines carrying terminal hydroxyl groups on the one hand and aliphatic or aromatic polyisocyanates on the other, well as precursors thereof.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylenediamine and isophthalic and/or terephthalic acid, with or without an elastomer as modifier, for example poly-2,4,4,-trimethylhexamethylene terephthalamide or poly-m-phenylene isophthalamide; block copolymers of the aforementioned polyamides with polyolefins, olefin copolymers, ionomers or chemically bonded or grafted elastomers; or with polyethers, for example with polyethylene glycol, polypropylene glycol or polytetramethylene glycol; and also polyamides or copolyamides modified with EPDM or ABS, and polyamides condensed during processing (RIM polyamide systems).

16. Polyureas, polyimides and polyamide-imides and polybenzimidazoles.

17. Polyesters derived from dicarboxylic acids and diols and/or from hydroxycarboxylic acids or the corresponding lactones, such as poly-ethylene terephthalate, polybutylene terephthalate, poly-1,4-dimethylocyclohexane terephthalate, polyhydroxybenzoates as well as block-copolyether esters derived from hydroxyl-terminated polyethers; and also polyesters modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins derived from substituted acrylic esters such as epoxy acrylates, urethane acrylates or polyester acrylates.

24. Alkyd resins, polyester resins or acrylate resins which are cross-linked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers such as cellulose, rubber, gelatine and chemically modified homologous derivatives thereof such as cellulose acetates, cellulose propionates and cellulose butyrates, or the cellulose ethers, such as methylcellulose; as well as rosins and their derivatives.

27. Mixtures (poly-blends) of the aforementioned polymers, for example PP/EPDM, Polyamide 6/EPDM or ABS, PVC/EVA, PVS/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

Most of the compounds of formula I are known compounds which are disclosed, for example, in U.S. Pat. Nos. 3,118,887 and 3,244,708 or in U.S. patent application Ser. No. 446,369.

The invention is illustrated in more detail by the following Examples in which parts and percentages are by weight, $\overline{M}_n$ is the molecular weight expressed as number average and $\overline{M}_w$ is the molecular weight expressed as weight average.

EXAMPLE 1

Incorporation by Polymer-Analogous Reaction a) Preparation of a functional polymer In a 6 liter glass flask, 2070 ml of dry toluene are heated to reflux under nitrogen. With stirring, solutions I and II are added simultaneously:

| Solution I: | 606.8 g of methyl methacryalte |
| --- | --- |
| | 1212.3 g of butyl methacrylate |
| | 631.5 g of glycidyl methacrylate |
| Solution II: | 60 g of azoisobuyronitrile |
| | 750 ml of toluene |

Solution I is added dropwise over 3 hours and solution II over 3.5 hours. The reaction mixture is then heated to reflux for 1 hour to give a viscous ca. 50% polymer solution which is clear and colourless. The solution contains 4.33 mol of epoxy groups.

b) Reaction with a triazine derivative 275 g of the above polymer solution are mixed with 4.5 g of 2,4-bis(2,4-dimethylphenyl)-6-(2,4-dihydroxyphenyl)-1,3,5-traizine in a glass flask and the mixture is heated for 48 hours to reflux (temperature in the reactor ca. 110° C.). In this reaction, the epoxy groups of solution I react with the hydroxyl groups of solution II. A pale yellow, clear solution of the modified polymer is obtained. Elemental analysis shows that the polymer contains 3.2% of the triazine compound. The molecular weight is $\overline{M}_n$ 4363 and $\overline{M}_w$ 13308 according to gel permeation chromatography.

c) Test of resistance to weathering

The solution of the modified acrylate resin is mixed in the solids ratio of 65:35 with a melamine resin (Cymel ® 327, Cyanamid Corp.). To this mixture are added 2.5% (based on solids) of a levelling agent (Baysilon ® A, Bayer AG) (1% solution in xylene).

This clear lacquer formulation is diluted with xylene/butanol/butyl glycol acetate 13:6:1 to a sprayable consistency, applied to an aluminium sheet which has been primed with a silver metallic primer lacquer, and stoved for 30 minutes at 130° C. The finish so obtained has a film thickness of 40–45 μm.

The clear lacquer described in a), which does not contain triazine, is used for comparison purposes. The resistance to weathering of the specimens is tested in a UVCON ® UVB-313 weatherometer at a cycle of 4 h UV radiation at 60° C. and 4 h condensation at 50° C. The 20° gloss according to DIN 67 530 before weathering and after 400 h weathering is determined.

| Incorporated stabiliser | 20° gloss (%) after | |
|---|---|---|
| | 0 | 400 h |
| none | 81 | 1 |
| 2.1% triazine | 83 | 61 |

EXAMPLE 2

Incorporation by Copolymerisation

A) 200 ml of dry xylene are heated to 135° C. in a 750 ml glass flask. With stirring, solutions III and IV are added dropwise simultaneously over 3 hours.

After the addition, the reaction mixture is heated for 1 hour to 135° C. to give a pale yellow, clear solution of Solution III:  75 g of butyl acrylate
 81 g of butyl methacrylate
 90 g of hydroxyethyl acrylate
 45 g of styrene
 9 g of glacial acetic acid
 18.6 g of tert-amyl perbenzoate Solution IV:  40 ml of xylene
 10.5 g of 1-methacryloyloxy-2-hydroxy-3-[4-(4,6-di[2,4-dimethyl phenyl]-3-triazin-2-yl)-3-hydroxyphenoxy]propane of formula

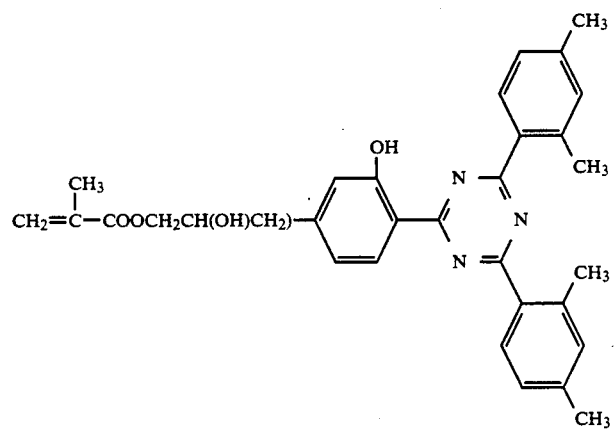

the copolymer. Elemental analysis shows that the copolymer contains 3.3% of the above triazine and has a molecular weight of $\overline{M}_n$ 3248 and $\overline{M}_w$ 8135.

B) The resin solution so obtained is mixed in the solids ratio of 65:35 with a melamine resin (Cymel ® 303, Cyanamid Corp.). To this mixture is added 0.5% (based on solids) of p-toluenesulfonic acid as curing catalyst.

This clear lacquer formulation is diluted with xylene to a sprayable consistency, applied to an aluminium sheet which has been primed with a silver metallic primer lacquer. The finish obtained after stoving (30 minutes at 120° C.) has a film thickness of 40–45 μm.

A clear lacquer which does not contain triazine, and which has been prepared by polymerisation of solution III and subsequent mixing with a melamine resin, is used for comparison purposes. The resistance to weathering of the specimens is tested in the UVCON ® weatherometer.

| Incorporated stabiliser | 20° gloss (%) after | | | | |
|---|---|---|---|---|---|
| | 0 | 400 | 1600 | 2400 | 3200 h |
| none | 90 | 83 | 18 | — | — |
| 2.1% triazine | 93 | 90 | 90 | 92 | 91 |

EXAMPLE 3

Simultaneous Incorporation of a Hindered Amine (HALS)

The procedure described in Example 2A) is repeated, except that 5.1 g of 4-acryloyloxy-1,2,2,6,6-pentamethylpiperidine are additionally added to solution IV. A pale yellow, viscous solution of the copolymer is obtained. The copolymer contains 3.3% of the triazine derivative and 1.6% of the piperidine derivative, and has a molecular weight of $\overline{M}_n$ 3063 and $\overline{M}_w$ 9283.

100 parts of the resin solution are mixed with 0.14 part of zinc octoate, 30 parts of trimerised diisocyanate (Desmodur ® 3390) and 1.6 parts of a levelling agent (Byk ® 300).

In the same manner, 100 parts of the resin solution of Example 2A are mixed with zinc octoate, Desmodur ® 3390 and Byk ® 300.

For comparison purposes, 100 parts of the polymer solution obtained (which contains no triazine) from solution III of Example 2A are mixed in the same manner with zinc octoate, Desmodur ® 3390 and Byk ® 300.

All three resin solutions are diluted with xylene to a sprayable consistency and applied to aluminium sheets which have been primed with a silver metallic primer lacquer. The specimens are stoved for 20 min. at 140° C. The film thickness obtained is 45–50 μm.

The resistance to weathering of the specimens is tested in the UVCON ® 313 at a cycle of 8 h UV irradiation at 70° C. and 4 h condensation at 50° C., and the 20° gloss is determined according to DIN 67 530.

| Incorporated stabilizer | 20° gloss (%) after | | | | |
|---|---|---|---|---|---|
| | 1600 | 2800 | 4000 | 6000 | 7600 h |
| none | 52 | 36*) | | | |
| 2.2% triazine | 84 | 78 | 74 | 58*) | |
| 2.2% triazine + 1.1% HALS | 89 | 83 | 81 | 63 | 52 |

*)cracking

EXAMPLE 4

Incorporation in a UV Curable System

A UV curable system is prepared from
66 parts of a urethane acrylate (Genomer ® T 1600, ex Mäder),
32 parts of 1,6-hexanediol diacrylate (Sartomer ® SR 238) and
2 parts of 1-benzoylcyclohexanol (as initiator).

One portion is mixed with 1.5% with the unsaturated triazine derivative described in Example 2. A second portion is mixed with 1.5% of this triazine derivative and 0.5% of 4-acryloyloxy-1-octyloxy-2,2,6,6-tetramethylpiperidine (HALS). A third portion is cured without the addition of stabiliser.

The formulations are applied to aluminium sheets which have been primed with a silver metallic primer lacquer, and cured in a UV processor (supplied by PPG) with 2 lamps of 80 W/cm in two passes at a speed of 10 m/mm. The finish obtained has a film thickness of ca. 40 μm.

The specimen sheets are subjected to weathering in a UVCON ® 313 at a cycle of 4 h UV irradiation at 60° C. and 4 h condensation at 50° C., and the 20° gloss is determined according to DIN 67 530.

| Incorporated stabiliser | 20° gloss (%) after | | | | |
|---|---|---|---|---|---|
| | 0 | 800 | 1600 | 2800 | 4000 h |
| none | 81 | 21*) | | | |
| 1.5% triazine | 80 | 88 | 85 | 68*) | |
| 1.5% triazine + 0.5% HALS | 82 | 88 | 88 | 87 | 82 |

*)cracking

EXAMPLE 5

Incorporation in a Photocurable System

A photocurable clear lacquer is prepared from 70 parts of an aliphatic urethane acrylate (Ebecryl ® 284, ex UCB) and 30 parts of 1,6-hexanediol bis(acrylate). To a portion of this lacquer is added 2% of the triazine derivative described in Example 2 (dissolved in xylene).

The test lacquers are applied to a white-primed aluminium sheet and irradiated in an electron beam apparatus at an intensity of 1 Mrad. The resultant finish has a film thickness of ca. 40 μm.

The incorporation of the triazine is verified by extracting a part of the specimen aluminium sheet for 2 hours with toluene and making an analytical investigation of the extract. The concentration of extracted triazine is less than 0.1%, thereby demonstrating the quantitative incorporation of triazine in the lacquer.

The specimens are subjected to weathering in the UVCON ® 313 as in Example 4, and the 20° gloss is determined.

| Incorporated stabiliser | 20° gloss (%) after | | | | |
|---|---|---|---|---|---|
| | 0 | 400 | 800 | 600 | 2400 h |
| none | 81 | 78 | 79*) | | |
| 2.0% triazine | 83 | 81 | 82 | 78 | 72 |

*)delamination

What is claimed is:
1. A process for incorporating an o-hydroxyphenyl-s-triazine in an organic polymer, which process comprises incorporating a compound of formula I

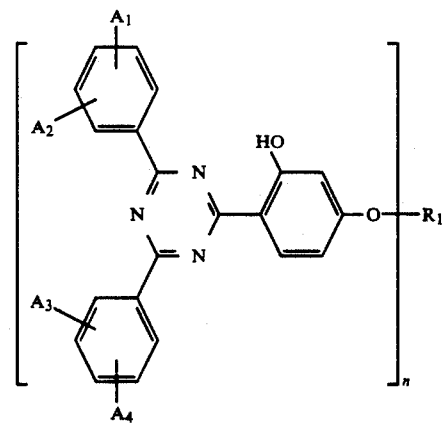

wherein
n is 1 or 2,
$A_1$, $A_2$, $A_3$ and $A_4$ are each independently of one another hydrogen, $C_1$–$C_{12}$alkyl, cyclohexyl or halogen, $R_1$, when n is 1, is hydrogen, $C_1$-$C_{18}$alkyl which is substituted by OH, —COOH, —COOR$_2$, —NHR$_3$, —CONHR$_4$,

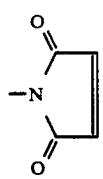

and/or —O—CO—R$_4$, $C_4$-$C_{20}$ alkyl which is substituted by OH and interrupted by one or more oxygen atoms, $C_2$-$C_4$alkyl which is substituted by OH and $C_1$-$C_{12}$alkoxy or phenoxy, cyclohexyl which is substituted by OH or —OCOR$_4$, or is $C_2$-$C_6$alkenyl, glycidyl or a group selected from

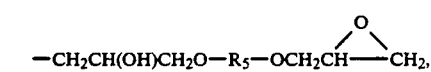

—CO—R$_6$—COOH or —CO—NH—R$_7$—NCO, and, when n is 2, is a group selected from —CH$_2$CH(OH)CH$_2$—, —CO—CH=CH—CO—, —CH$_2$CH(OH)CH$_2$O—R$_5$—OCH$_2$CH(OH)CH$_2$— or —CH$_2$CH(R$_8$)O—CO—CH=CH—CO—OCH(R$_8$)CH$_2$—, $R_2$ is $C_1$-$C_4$alkyl, glycidyl or $C_3$-$C_5$alkenyl,
$R_3$ is hydrogen, $C_1$-$C_{12}$alkyl, $C_3$-$C_5$alkenyl or cyclohexyl,
$R_4$ is $C_2$-$C_6$alkenyl or $C_2$-$C_6$hydroxyalkyl,
$R_5$ is $C_2$-$C_{10}$alkylene, phenylene or a group

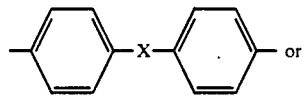

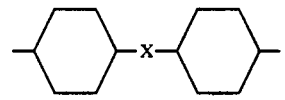

wherein X is —O—, —S—, —SO$_2$, —CH$_2$— or —C(CH$_3$)$_2$—, or R$_5$ is a group —CO—R$_9$—CO—,
$R_6$ is $C_2$-$C_{14}$alkylene, —CH=CH— or o-phenylene,
$R_7$ is $C_2$-$C_{10}$alkylene, phenylene, tolylene or a group of formula

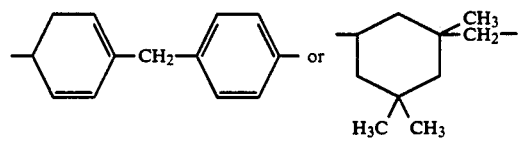

$R_8$ is hydrogen or methyl, and
$R_9$ is $C_2$-$C_{10}$alkylene, —CH=CH— or phenylene, either during the synthesis of the polymer by copolymerisation, copolycondensation or copolyaddition, or by reaction with a polymer which contains suitable functional groups.

3. A process according to claim 1, which comprises incorporating a compound of formula I, wherein n is 1 or 2, $A_1$, $A_2$, $A_3$ and $A_4$ are hydrogen, $C_1$-$C_4$alkyl or chloro,
$R_1$, when n is 1, is hydrogen, $C_1$-$C_4$alkyl which is substituted by OH, —COOH, —COOR$_2$, —NHR$_3$, —CONHR$_4$ and/or —O—CO—R$_4$, $C_4$-$C_{20}$alkyl which is substituted by OH and interrupted by one or more oxygen atoms, propyl which is substituted by OH and $C_1$-$C_{12}$alkoxy or phenoxy, cyclohexyl which is substituted by OH or —OCOR$_4$, or is allyl, glycidyl or a

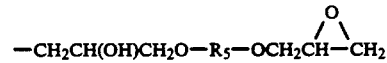

or —CO—NH—R$_7$—NCO group, and, when n is 2, is a group selected from —CH$_2$CH(OH)CH$_2$—, —CH$_2$CH(OH)CH$_2$O—R$_5$—OCH$_2$CH(OH)CH$_2$— or —CH$_2$CH(R$_8$)O—CO—CH=CH—CO—OCH(R$_8$)CH$_2$—, $R_2$ is $C_1$-$C_4$alkyl, glycidyl or allyl,
$R_3$ is $C_1$-$C_{12}$alkyl,
$R_4$ is $C_2$-$C_6$alkenyl,
$R_5$ is $C_2$-$C_{10}$alkylene, phenylene or a

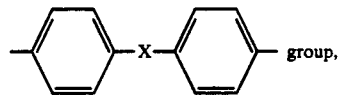

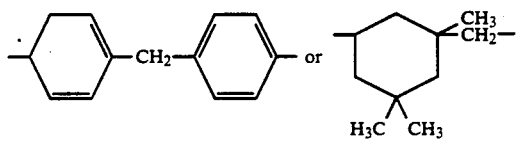

wherein X is —O—, —S—, —SO$_2$, —CH$_2$— or —C(CH$_3$)$_2$—, or R$_5$ is a —CO—R$_9$—CO— group,
$R_7$ is $C_2$-$C_{10}$alkylene, phenylene, tolylene or a group of formula

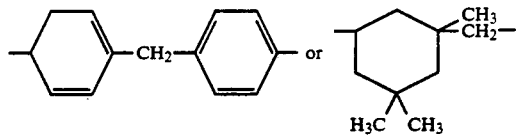

$R_8$ is hydrogen or methyl, and
$R_9$ is $C_2$-$C_{10}$alkylene, —CH=CH— or phenylene.

3. A process according to claim 1, which comprises incorporating a compound of formula I, wherein n is 1 or 2,
$A_1$ and $A_3$ are hydrogen, methyl or chloro,
$A_2$ and $A_4$ are hydrogen or methyl,
$R_1$, when n is 1, is hydrogen, $C_1$-$C_4$alkyl which is substituted by OH, —COOH, —COOR$_2$ and/or —O—CO—R$_4$, $C_4$-$C_{20}$alkyl which is substituted by OH and interrupted by one or more oxygen atoms, propyl which is substituted by OH and $C_4$-$C_{12}$alkoxy, or is glycidyl, allyl, or a

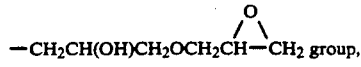

and, when n is 2, is a —CH$_2$CH(OH)CH$_2$— or —CH$_2$CH(OH)CH$_2$O—R$_5$—OCH$_2$CH(OH)CH$_2$— group,
R$_2$ is C$_1$-C$_4$alkyl or allyl bedeutet,
R$_4$ is C$_2$-C$_4$alkenyl, and
R$_5$ is C$_4$-C$_8$alkylene or

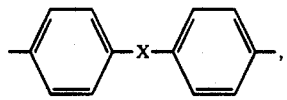

wherein X is —CH$_2$— or —C(CH$_3$)$_2$—.

4. A process according to claim 1, which comprises copolymerising a compound of formula I, wherein n is 1 or 2, R$_1$, when n is 1, is C$_2$-C$_6$alkenyl, C$_1$-C$_{18}$alkyl which is subsituted by —COOR$_2$, —NH—R$_3$, —CONHR$_4$ or —O—CO—R$_4$, cyclohexyl which is substituted by —O—CO—R$_4$, or is a —CO—CH=CH—COOH group, and, when n=2, is group selected from —CO—CH=CH—CO—, —CH$_2$CH(R$_8$)O—CO—CH=CH—CO—OCH(R$_8$)CH$_2$— or —CH$_2$CH(OH)CH$_2$O—CO—CH=CH—CO—OCH$_2$CH(CH)CH$_2$—, R$_2$ is C$_3$-C$_5$alkenyl, R$_3$ is allyl, R$_4$ is C$_2$-C$_6$alkenyl, and R$_8$ is hydrogen or methyl, with one or more ethylenically unsaturated monomers.

5. A process according to claim 4, which comprises copolymerising a compound of formula I, wherein R$_1$ is allyl, C$_1$-C$_4$alkyl which is substituted by —COOR$_2$ or —O—CO—R$_4$, or cyclohexyl which is substituted by —O—CO—R$_4$, R$_2$ is allyl, and R$_4$ is C$_2$-C$_4$alkenyl, with one or more ethylenically unsaturated monomers.

6. A process according to claim 4, wherein the monomers are selected from acrylic acid, methacrylic acid, esters or amides of acrylic acid or methacrylic acid, styrene and acrylonitrile.

7. A process according to claim 1, which comprises incorporating a compound of formula I, wherein n is 1 or 2, R$_1$, when n is 1, is C$_1$-C$_{18}$alkyl which is substituted by OH and —COOH, —COOR$_2$ or —NHR$_3$, or is a —CH$_2$CH(OH)CH$_2$OH or

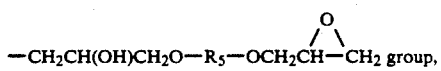

and, when n is 2, is a —CH$_2$CH(OH)CH$_2$O—R$_5$—OCH$_2$CH(OH)CH$_2$— group, R$_2$ is C$_1$-C$_4$alkyl, R$_3$ is hydrogen, C$_1$-C$_{12}$alkyl, allyl or cyclohexyl, and R$_5$ is C$_2$-C$_{10}$alkylene, phenylene or a group

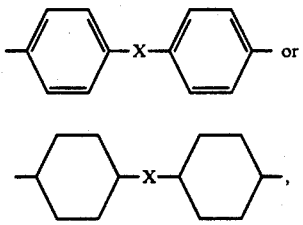

wherein X is —O—, —S—, —SO$_2$—, —CH$_2$ or —CH(CH$_3$)$_2$—, by copolycondensation or copolyaddition, in a polyester or polyether ester, a polyamide, polyurethane, polycarbonate, epoxy resin, phenolic resin, melamine resin or alkyd resin.

8. A process according to claim 1, which comprises incorporating a compound of formula I, wherein n is 1, R$_1$ is hydrogen, C$_1$-C$_{18}$alkyl which is substituted by OH, —COOH, —COOR$_2$, —NHR$_3$, —CONHR$_4$ or —O—CO—R$_4$, C$_4$-C$_{20}$alkyl which is substituted by OH and interrupted by one or more oxygen atoms, C$_2$-C$_4$-Alkyl which is substituted by OH and C$_1$-C$_{12}$alkoxy or phenoxy, OH-substituted cyclohexyl, or is glycidyl or a —CO—R$_6$—COOH or —CO—NH—R$_7$—NCO group, R$_2$ is C$_1$-C$_4$alkyl or glycidyl, R$_3$ is hydrogen, C$_1$-C$_{12}$alkyl or cyclohexyl, R$_4$ is C$_2$-C$_6$hydroxyalkyl, R$_6$ is C$_2$-C$_{14}$alkylene, —CH=CH— or o-phenylene, and R$_7$ is as defined in claim 1, by copolycondensation or copolyaddition, in a polyester or polyether ester, a polyamide, polyurethane, polycarbonate, epoxy resin, phenolic resin, melamine resin or alkyd resin.

9. A process according to claim 1, which comprises reacting a polymer which contains hydroxyl, carboxyl, anhydride, amino, epoxy or isocyanato groups with a compound of formula I which contains such functional groups which are able to react with the functional groups of the polymer.

10. A process according to claim 9, which comprises reacting a polymer which contains OH groups with a compound of formula I which contains at least one isocyanato, epoxy, carboxyl or ester group.

11. A process according to claim 9, which comprises reacting a polymer which contains epoxy groups with a compound of formula I which contains at least one hydroxyl, carboxyl or amino group.

12. A process according to claim 1, which comprises grafting an ethylenically unsaturated compound of formula I as defined in claim 4 on to a hydrocarbon polymer.

13. A process according to claim 12, which comprises grafting an ethylenically unsaturated compound of formula I as defined in claim 4 on to a polyolefin.

14. A polymer modified by a process as claimed in claim 1 and containing 0.05 to 50% by weight of a triazine compound of formula I chemically bound to said polymer.

15. A polymer according to claim 14 and containing 0.05 to 5% by weight of a compound of formula I chemically bound to said polymer.

16. A polymer according to claim 14 and containing 5 to 50% by weight of a compound of formula I chemically bound to said polymer.

17. A modified polymer in the form of microparticles according to claim 14 and containing 0.1 to 30% by weight of a compound of formula I chemically bound to said polymer.

18. A modified polymer according to claim 14, which is a copolymer of esters of acrylic or methacrylic acid, which copolymer may additionally contain acrylic or methacrylic acid as comonomer.

19. A modified polymer according to claim 14, which contains at least one stabiliser, a processing auxiliary, a pigment or another additive as physical modifier.

20. A modified polymer according to claim 19, which contains at least one stabiliser in an amount of 0.05 to 5% by weight.

21. A modified polymer according to claim 20, which contains a sterically hindered amine as physical modifier.

22. A modified polymer according to claim 14, which contains a sterically hindered amine incorporated therein.

23. A coating composition comprising as the binder therein a polymer according to claim 15.

24. A method for stabilizing an organic material which comprises incorporating therein an effective stabilizing amount of a polymer according to claim 16.

25. The method of claim 24, wherein said organic material is an organic polymer.

* * * * *